(12) United States Patent
Morris et al.

(10) Patent No.: US 11,278,685 B2
(45) Date of Patent: Mar. 22, 2022

(54) INHALER

(71) Applicant: Kind Consumer Limited, London (GB)

(72) Inventors: Stephen Wynford Morris, Sussex (GB); David Hackett, Kent (GB)

(73) Assignee: KIND CONSUMER LIMITED, London (GB)

( * ) Notice: Subject to any disclaimer, the term of this patent is extended or adjusted under 35 U.S.C. 154(b) by 550 days.

(21) Appl. No.: 15/999,431

(22) PCT Filed: Feb. 13, 2017

(86) PCT No.: PCT/GB2017/050377
§ 371 (c)(1),
(2) Date: Aug. 17, 2018

(87) PCT Pub. No.: WO2017/141018
PCT Pub. Date: Aug. 24, 2017

(65) Prior Publication Data
US 2021/0204615 A1   Jul. 8, 2021

(30) Foreign Application Priority Data
Feb. 19, 2016 (GB) ..................................... 1602939

(51) Int. Cl.
*A61M 15/00* (2006.01)
*A24F 42/20* (2020.01)
(Continued)

(52) U.S. Cl.
CPC ......... *A61M 15/0091* (2013.01); *A24F 42/10* (2020.01); *A24F 42/20* (2020.01); *A24F 42/60* (2020.01); *A61M 15/06* (2013.01)

(58) Field of Classification Search
None
See application file for complete search history.

(56) References Cited

U.S. PATENT DOCUMENTS

2009/0133692 A1* 5/2009 Abrams ............ A61M 15/0038
128/200.21
2009/0151716 A1* 6/2009 Abrams ............ A61M 15/0041
128/200.14

FOREIGN PATENT DOCUMENTS

GB          2519950 A       5/2015
GB          2528068 A       1/2016
(Continued)

OTHER PUBLICATIONS

International Search Report and Written Opinion dated Apr. 21, 2017 for Application No. PCT/GB2017/050377.
(Continued)

*Primary Examiner* — Francisco W Tschen
*Assistant Examiner* — Guy F Mongelli
(74) *Attorney, Agent, or Firm* — Patterson + Sheridan, LLP

(57) ABSTRACT

An inhaler comprising an elongate housing containing a reservoir of inhalable composition. An outlet for the composition and suction port are provided at one end of the housing. A diaphragm is mounted in the housing defining a suction chamber such that suction on the suction port reduces the size of the suction chamber. An elongate leaf spring is mounted at one end to the housing at the end of the suction chamber opposite to the suction port, and is pivotally mounted at an intermediate portion about a pivot point. A valve element is at the end of the leaf spring opposite to the one end and is biased closed. Suction on the suction port deflects the diaphragm and hence the leaf spring between the one end and the pivot point causing the opposite end of the leaf spring to pivot about the pivot point thereby causing the valve element to open.

11 Claims, 2 Drawing Sheets

(51) Int. Cl.
*A24F 42/60* (2020.01)
*A24F 42/10* (2020.01)
*A61M 15/06* (2006.01)

(56) References Cited

FOREIGN PATENT DOCUMENTS

| WO | 2011015825 A1 | 2/2011 |
| WO | 2011015826 A1 | 2/2011 |

OTHER PUBLICATIONS

United Kingdom Search Report dated Jul. 12, 2016 for Application No. GB1602939.9.

\* cited by examiner

INHALER

The present invention relates to an inhaler.

In particular, the present invention relates to an inhaler of the type disclosed in WO 2011/015825. Such an inhaler is primarily intended as a simulated cigarette. However, it can be used as a dispensing mechanism for various orally inhalable medicaments.

The inhaler comprises an elongate housing containing a pressurised reservoir of inhalable composition. An outlet for the composition is provided at one end of the housing. An outlet flow path is provided from the reservoir to the outlet and a valve element is biased into a closed position in which it prevents flow from the reservoir.

Similar inhalers are disclosed in WO 2011/015826, WO 2014/033438 and WO 2014/033439.

With the current design, the majority of the inhaler is produced as a one-piece plastics moulding. The valve element itself is part of a separate moulding which includes a vane and a diaphragm. There is then a coiled spring which is inserted into the top of the vane and bears against a cap which is fitted over the top of the vane and the diaphragm.

The present invention is directed to an improvement of such an inhaler which is more suited to mass production techniques.

According to the present invention there is provided an inhaler as defined in claim 1.

The present invention makes use of a leaf spring which is located at one end with respect to the housing and at a pivot point which is also part of the housing. Both of these points of location of the spring are part of the housing and can therefore be part of a single moulding. As such, the positions of the two mounting points can be precisely and reliably set as they can be formed as features of the mould. This contrasts with the previous design where the vane was part of a separate component which is fitted into the housing and the spring was a separate component again which bears against a fourth component, namely the cap. Reliable operation of the inhaler relies on accurately locating all four of the components which, if it is not done carefully, will result in the possibility of accumulated tolerance errors which can provide an unacceptable rejection rate. With the present invention, all that is required is for the leaf spring to be correctly located in two positions which are defined by a moulding process such that there is not the same potential to build up tolerance errors. While the device may be provided with a cap in order to complete the inhaler assembly, the positioning of this cap has no bearing on the functioning of the valve. Further, no part of the spring bears against the cap so that the requirement for the cap to be sonically welded in place to accommodate the biasing force of the spring as in the prior art device is eliminated.

Further, the provision of a leaf spring in place of the coil spring of the prior art also helps facilitate the manufacturing process as the leaf spring is easier to handle that the small coiled springs which can easily become tangled up with one another and are awkward to insert in a small opening in the vane.

The pivotal mounting of the intermediate portion of the leaf spring may be provided by a separate pivot pin inserted through an opening in the leaf spring which may be provided, for example, by punching an indent into the leaf spring to create a passage for the pivot pin. Alternatively, the pivotal mounting is made via a projection on the leaf spring, for example a pair of laterally extending lugs. This removes the need for the pivot pin thereby reducing the component count and eliminating the awkward step of threading the pivot pin through a small orifice.

In order to enhance the mechanical advantage provided by the leaf spring, the pivot point is preferably closer to the opposite end of the leaf spring than the one end. Preferably, it is at least two thirds of the way along the spring from the one end to the opposite end. This ensures that a relatively high biasing force can be provided to close the valve, but this can be overcome with the relatively small inhaling force thereby allowing the device to operate satisfactorily at the type of inhalation flow rate typically associated with real cigarettes.

The leaf spring between the one end and the pivot point is preferably upwardly bowed when no suction is applied to the suction port thereby generating the biasing force on the valve element. This provides a convenient way of achieving the biasing force. The leaf spring may be a pre-stressed leaf spring such as that disclosed in U.S. Pat. No. 4,796,355 (FIG. 13). This is a bi-stable spring which will provide a quicker transition between a fully open and a fully closed condition. This may be useful in certain applications although other applications such as a simulated cigarette would benefit from a more gradual transition between the two positions as provided by a non pre-stressed leaf spring.

The valve element may be a separate component attached to the opposite end of the leaf spring. However, preferably, it is an extension of the leaf spring itself. This reduces the number of components required. It may simply be the flat end of the leaf spring. However, preferably, the valve element is provided by a downwardly bent portion of the leaf spring.

The inhaler preferably has at least one airflow path in the form of an air inlet in the housing and an air outlet at the one end of the housing. This allows the draw force on the inhaler to be set independently of the suction force required to open the valve thereby allowing greater freedom to realistically mimic the operation of a real cigarette. Preferably the airflow path is positioned to impinge on the composition plume leaving the composition outlet thereby reducing the particle size of the plume.

An example of an inhaler in accordance with the present invention will now be described with reference to the accompanying drawings, in which.

Figure 1:
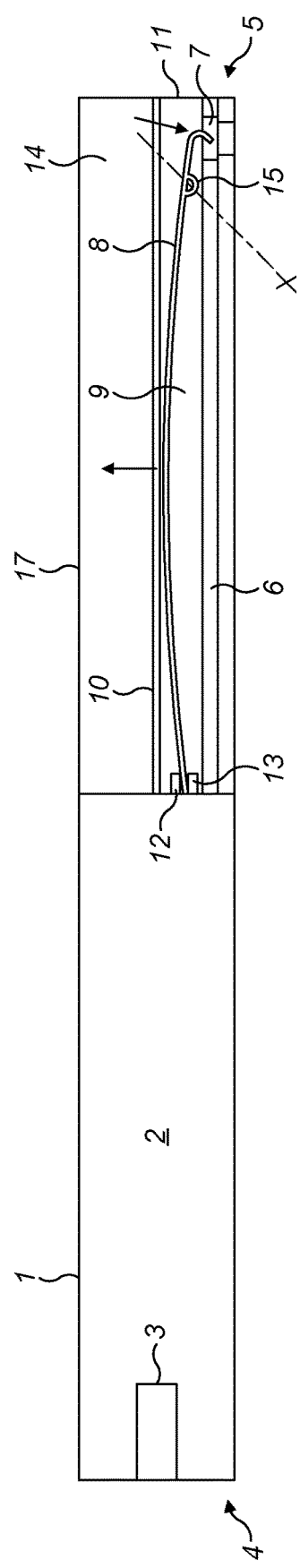
FIG. 1 is a schematic cross-section of the inhaler with the valve closed.

The general design of the inhaler is broadly as disclosed in WO 2011/015825, WO 2011/015826, WO 2014/033438 and WO 2014/033439.

Thus, the inhaler is intended to be the same size and shape as a cigarette, although other shapes and configurations are possible. It comprises a housing 1 containing a reservoir 2 of a pressurised composition. A refill valve 3 is provided at the refill 4 of the inhaler with the opposite end 5 being the inhaling end. A delivery tube 6 effectively represents an extension of the reservoir 2 which extends almost all of the way to the outlet end 5. A deformable pinch tube 7 is provided in the delivery tube 6 in the vicinity of the outlet end 5. This is a small elastomeric tube with an outlet orifice at the end adjacent to the outlet end 5. The pinching of this tube selectively prevents and allows the dispensing of the composition from the pressurised reservoir. As an alternative to a pinch tube, a gate valve could be provided. Thus far, the inhaler as described is the same as in the four abovereferenced applications. The difference provided by the present invention is the manner in which the valve is selectively opened.

This is done by a leaf spring 8 as described below. The leaf spring 8 has an elongate configuration which is mounted to extend longitudinally within a suction chamber 9. This chamber is defined above the delivery tube 6 and beneath a flexible diaphragm 10. The suction chamber 9 has a suction port 11 at the outlet end. Suction on the outlet end 5 causes the diaphragm 10 to deflect downwardly (as shown in FIG. 2).

The leaf spring 8 has a mounting end 12 mounted in a groove 13. An intermediate portion 14 of the spring is mounted at a pivot point 15 so as to pivot about an axis X perpendicular to a longitudinal direction of the inhaler.

This pivotal mounting may take a number of forms. One possibility is that a central portion of the leaf spring 8 is pressed downwardly to create a loop though which a separate pivot pin is inserted. This pivot pin is then mounted on opposite sides of the leaf spring in lugs (not shown) which are an integral moulding with the housing 1. Alternatively, the pivot may be provided by a pair of laterally extending projections which are integral with the leaf spring 8 and which are mounted in similar lugs in the housing.

Figure 2:
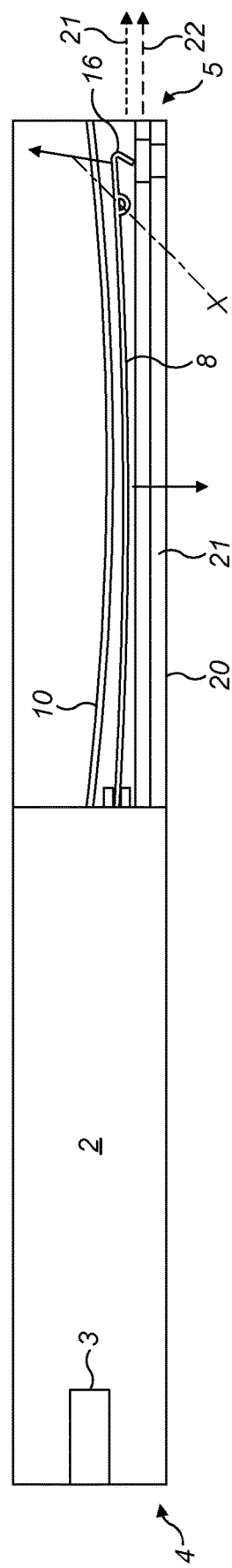
FIG. 2 is a similar view with the valve open.

As will be appreciated from FIGS. 1 and 2, the leaf spring 8 in the closed configuration is biased in an upwardly bowed configuration, this being the configuration to which it will return in the absence of any additional force. The biased nature of the mounting causes the valve end 16 of the leaf spring (opposite to the mounting end 12) to be biased downwards thereby pinching the tube 7 closed. It will also be appreciated that the pivot point 15 is very close to the valve end 16 of the leaf spring 8 with it being positioned some 90% of the way along leaf spring 8 as measured from the mounting end 12.

The effect of this is that a relatively large deflection of an intermediate portion of the spring 8 (between the mounting end 12 and pivot point 15) caused by the pressure of the diaphragm 10 deflects the leaf spring 8 from the upwardly bowed configuration as shown in FIG. 1 to the downwardly bowed configuration as shown in FIG. 2. This produces a relatively small movement of the valve end 16 of the spring which is the portion that presses on the tube 7. This mechanical advantage provided by the spring allows a high clamping force of the spring to be accommodated thereby providing a strong closure force. However, this mechanical advantage also means that this relatively large closure force can be overcome with a relatively small inhalation force. This means that the inhaler can be operated at a suction pressure which is close to a typical inhalation pressure of a cigarette.

The inhaler also comprises an airflow path with at least one air opening inlet 20 beneath the tube 6. This leads to an airflow path 21 running parallel to the tube 6 which exists the inhaler at the outlet end as depicted by arrow 21 in the vicinity of a composition plume 22 emitted from the tube 7.

Figure 3:
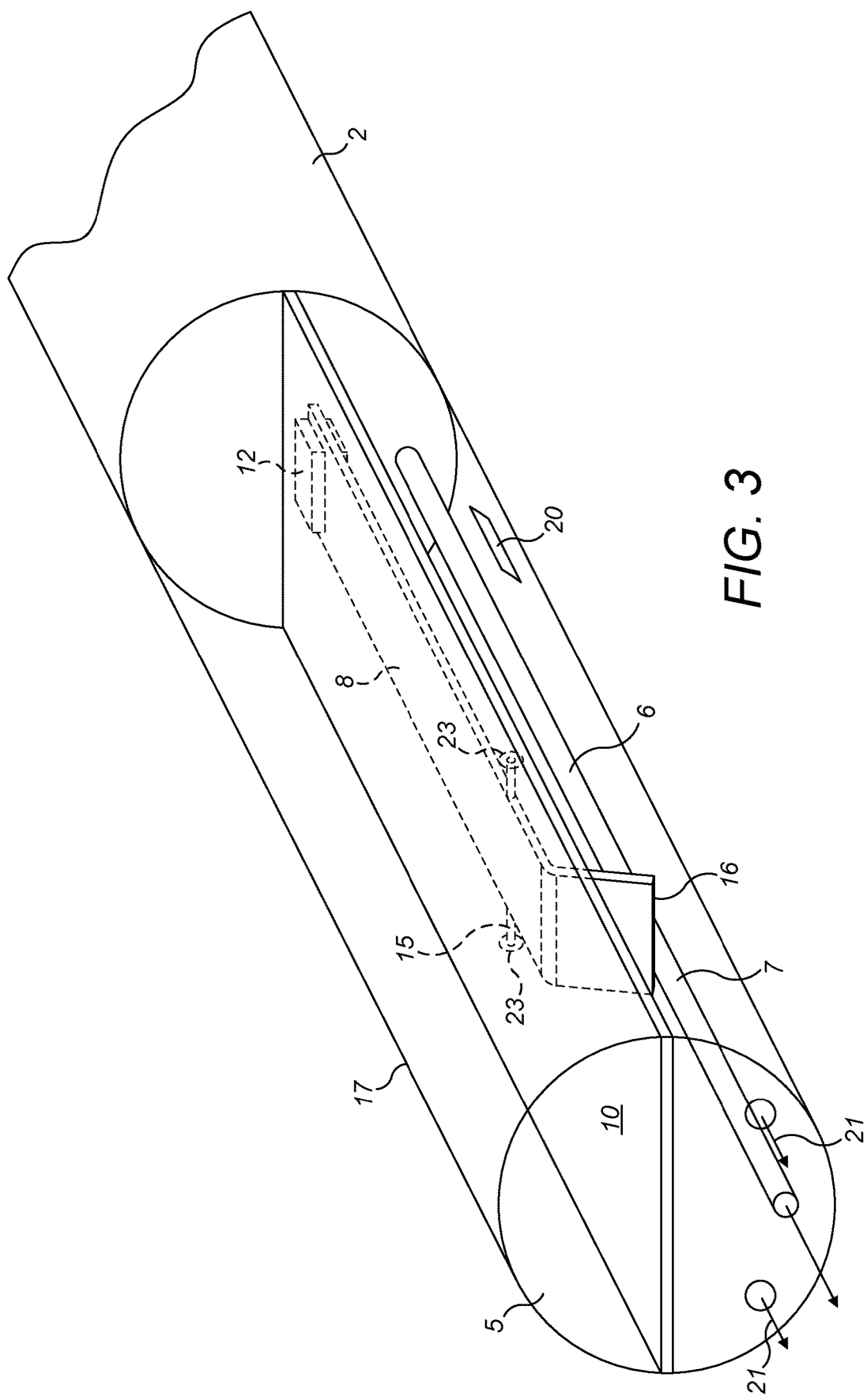
FIG. 3 is a schematic perspective view of the inhaler in an intermediate position.

The majority of the housing 1 is formed as a one-piece moulding. This includes the portion surrounding the reservoir 2 and, the portion forming the suction chamber and the delivery tube 6 itself. This same moulding includes the groove 13 and the lugs 23 (shown schematically in FIG. 3) for the pivot point. The diaphragm 10 is simply a flexible sheet of polymer which is bonded to this housing whereupon a cap 17 is fitted over the top of the diaphragm to complete the housing. In the previous inhalers, the cap was required to be sonically welded in place as the spring acted against the cap to provide a biasing force. With the present configuration, there is no biasing force on the cap such that it is not required to be fixed in place. There may be some form of snap fit for the cap which temporarily retains it in place, but ultimately the intention is to wrap the inhaler in a paper-like wrap such that this intermediate welding step can be eliminated. Because the grooves 13 and lugs providing the pivot point 15 are features of the same moulded components, these can be precisely positioned. This means that the end 16 of the spring forming the valve element is reliably located at a position above the deformable tube 7 and is precisely mounted such that its biasing force can be reliably and predictably delivered.

The invention claimed is:

1. An inhaler comprising:
   an elongate housing containing a reservoir of inhalable composition;
   an outlet for the composition at one end of the housing;
   an outlet flow path from the reservoir to the outlet;
   a valve element being biased into a closed position in which the valve element prevents flow from the reservoir;
   a suction port in the one end of the housing;
   a diaphragm mounted in the housing defining a suction chamber defined on one side of the diaphragm, the suction chamber being in communication with the suction port, such that suction on the suction port reduces the size of the suction chamber; and
   an elongate leaf spring mounted to extend longitudinally in the suction chamber mounted to extend longitudinally in the suction chamber, the leaf spring being mounted at one end to the housing at the end of the suction chamber opposite to the suction port, and being pivotally mounted about a pivot point to the housing at an intermediate portion of the leaf spring, the valve element being at the end of the leaf spring opposite to the one end;
   wherein suction on the suction port is arranged to deflect the diaphragm and hence the leaf spring between the one end and the pivot point causing the opposite end of the leaf spring to pivot about the pivot point thereby causing the valve element to open the flow path.

2. An inhaler according to claim 1, further comprising a cap placed on the reservoir, a wrap surrounding the housing and cap, the wrap being primarily responsible for retaining the cap in place in the housing.

3. An inhaler according to claim 1, wherein the pivotal mounting is provided by a separate pivot pin inserted through an opening in the leaf spring.

4. An inhaler according to claim 1, wherein the pivotal mounting is made via a projection on the leaf spring.

5. An inhaler according to claim 1, wherein the pivot point is closer to the end of the elongate leaf spring opposite to the one end.

6. An inhaler according to claim 5, wherein the pivot point is at least two thirds of the distance along the spring from the one end to the opposite end.

7. An inhaler according to claim 1, wherein the leaf spring, between the one end and the pivot point is upwardly bowed when no suction is applied at the suction port thereby generating the biasing force on the valve element.

8. An inhaler according to claim 1, wherein the valve element is an extension of the leaf spring.

9. An inhaler according to claim 8, wherein the valve element is provided by a downwardly bent portion of the leaf spring.

10. An inhaler according to claim 1, further comprising at least one airflow path in the form of an air inlet in the housing and an air outlet at the one end of the housing.

11. An inhaler according to claim 10, wherein the airflow path is positioned to impinge on a composition plume leaving the composition outlet thereby reducing the particle size of the plume.

\* \* \* \* \*